(12) United States Patent
Dadsetan et al.

(10) Patent No.: US 8,343,527 B2
(45) Date of Patent: Jan. 1, 2013

(54) PHOTOCROSSLINKABLE OLIGO(POLY (ETHYLENE GLYCOL) FUMARATE) HYDROGELS FOR CELL AND DRUG DELIVERY

(76) Inventors: Mahrokh Dadsetan, Rochester, MN (US); Michael Yaszemski, Rochester, MN (US); Lichun Lu, Rochester, MN (US)

( * ) Notice: Subject to any disclaimer, the term of this patent is extended or adjusted under 35 U.S.C. 154(b) by 646 days.

(21) Appl. No.: 11/909,241

(22) PCT Filed: Mar. 23, 2006

(86) PCT No.: PCT/US2006/010629
§ 371 (c)(1),
(2), (4) Date: Sep. 11, 2009

(87) PCT Pub. No.: WO2006/102530
PCT Pub. Date: Sep. 28, 2006

(65) Prior Publication Data
US 2010/0055186 A1 Mar. 4, 2010

Related U.S. Application Data

(60) Provisional application No. 60/664,540, filed on Mar. 23, 2005.

(51) Int. Cl.
*A61F 2/00* (2006.01)
*A61K 9/14* (2006.01)
*C08F 2/48* (2006.01)
*C07K 14/51* (2006.01)

(52) U.S. Cl. ......... 424/423; 424/486; 522/167; 514/8.8; 514/7.6

(58) Field of Classification Search .............. 424/93.7, 424/486, 422; 522/167; 514/7.6, 8.8
See application file for complete search history.

(56) References Cited

U.S. PATENT DOCUMENTS 5,786,217 A * 7/1998 Tubo et al. ............... 435/402
5,908,782 A * 6/1999 Marshak et al. ........... 435/366

FOREIGN PATENT DOCUMENTS
EP 0 877 033 A1 * 11/1998

OTHER PUBLICATIONS

Temenoff et al. ("Thermally Cross-Linked Oligo(poly(ethylene glycol) fumarate) Hydrogels Support Osteogenic Differentiation of Encapsulated Marrow Stromal Cells in Vitro" in Biomacromolecules 2004, 5, 5-10, published online on Nov. 26, 2003).*

(Continued)

*Primary Examiner* — Blessing Fubara

(57) ABSTRACT

The invention provides photocrosslinkable, injectable, biodegradable oligo(poly(ethylene glycol) fumarate) (OPF) hydrogels made from the photopolymerization of an OPF macromer with UV light and a photoinitiator. Hydrogels with varying mechanical properties and water content can be made with changes in macromer and crosslinking agent concentration in a precursor solution. The biodegradable OPF hydrogels can be injected as a fluid into a bodily defect of any shape, may incorporate various therapeutic agents, e.g., cells and/or growth factors, and may be implanted via minimally invasive arthroscopic techniques.

18 Claims, 12 Drawing Sheets

OTHER PUBLICATIONS

Shin et al. ("In vivo bone and soft tissue response to injectable, biodegradable oligo(poly(ethylene glycol) fumarate) hydrogels," in Biomaterials 24 (2003) 3201-3211).*

Holland et al. ("In vitro release of transforming growth factor-b1 from gelatin microparticles encapsulated in biodegradable, injectable oligo(poly(ethylene glycol) fumarate) hydrogels," in Journal of Controlled Release 91 (2003) 299-313).*

Yang et al. ("The Design of Scaffold for Use in Tissue Engineering. Part I, Traditional Factors," in Tissue Engineering, vol. 7, No. 6, 2001).*

Behravesh et al. "Three-dimensional culture of differentiating marrow stromal osteoblasts in biomimetic poly(propylene fumarate-co-ethylene glycol)-based macroporous hydrogels," in Journal of Biomedical Material Research Part A, Aug. 6, 2003, pp. 698-703).*

Jo et al. ("Modification of Oligo(poly(ethylene glycol) fumarate Macromer with GRGD Peptide for the preparation of functionalized Polymer Networks" in Biomacromolecules 24 (2001), 255-261).*

Shin et al. ("In vivo bone and soft tissue response to injectable, biodegrdable oligo(poly(ethylene glycol) fumarate hydrogels" in Biomaterials 24 (2003) 3201-3211).*

International Search Report and Written Opinion under date of mailing of Aug. 24, 2006 in connection with International Patent Application No. PCT/US2006/010629.

* cited by examiner

PHOTOCROSSLINKABLE OLIGO(POLY (ETHYLENE GLYCOL) FUMARATE) HYDROGELS FOR CELL AND DRUG DELIVERY

CROSS-REFERENCES TO RELATED APPLICATIONS

This application claims priority from U.S. Provisional Patent Application No. 60/664,540 filed Mar. 23, 2005.

STATEMENT REGARDING FEDERALLY SPONSORED RESEARCH

This invention was made with government support under AR045871 and EB003060 awarded by the National Institute of Arthritis and Musculoskeletal and Skin Disease and the National Institute of Biomedical Imaging and Bioengineering. The government has certain rights in the invention.

BACKGROUND OF THE INVENTION

1. Field of the Invention

This invention relates to photocrosslinkable, injectable, biodegradable oligo(poly(ethylene glycol) fumarate) (OPF) hydrogels made from the photopolymerization of an OPF macromer with UV light and a photoinitiator. Hydrogels with varying mechanical properties and water content can be made with changes in macromer and crosslinking agent concentration in a precursor solution. The biodegradable OPF hydrogels can be injected as a fluid into a bodily defect of any shape, may incorporate various therapeutic agents, e.g., cells and/or growth factors, and may be implanted via minimally invasive arthroscopic techniques.

2. Description of the Related Art

Controlled release of bioactive molecules such as growth factors has become an important aspect of tissue engineering because it allows modulation of cellular function and tissue formation at the afflicted site. The encapsulation of drugs, proteins and other bioactive molecules within degradable materials is an effective way to control the release profile of the contained substance.

Accordingly, there is continued interest in providing injectable, photocrosslinkable and biodegradable systems for cell and drug delivery. Photopolymerizable, degradable biomaterials provide many advantages over chemically initiated thermoset systems. Photoinitiated reactions provide rapid polymerization rates at physiological temperatures. Further, because the initial materials are liquid solutions, the systems are easily placed in complex shaped volumes and subsequently reacted to form a polymer of exactly the required dimensions.

In this approach, the invasiveness of some surgical techniques is minimized as prepolymers are introduced to the desired site via injection and photocured in situ with fiber optic cables using arthroscopic techniques. (See, Anseth et al., "In situ forming degradable networks and their application in tissue engineering and drug delivery", *J Control Release*, 2002; 78(1-3):199-209.) In addition, by exposing the mixture of macromer and photoinitiator to the light source, the macromer undergoes rapid crosslinking and forms a network. (See, Bryant et al., "Cytocompatibility of UV and visible light photoinitiating systems on cultured NIH/3T3 fibroblasts in vitro", *J Biomater Sci Polym Ed.*, 2000; 11(5):439-57.) These networks can be used to entrap water-soluble drugs and enzymes and deliver them at a controlled rate. (See, Bryant et al., "Encapsulating chondrocytes in degrading PEG hydrogels with high modulus: engineering gel structural changes to facilitate cartilaginous tissue production", *Biotechnol Bioeng* 2004 86(7):747-55; and Hatefi et al., "Biodegradable injectable in situ forming drug delivery systems" *J Control. Release* 2002; 80(1-3):9-28.)

One tissue engineering application that has received significant interest is the restoration of defects in cartilage. Cartilage is one of the few tissues found in the body that has limited capability to regenerate as a result of injury, congenital abnormalities or arthritis. In the past decade, many research efforts have been devoted to orthopedic tissue engineering to produce methods that restore defects in the cartilage. (See, Anseth et al., "In situ forming degradable networks and their application in tissue engineering and drug delivery", *J Control Release* 2002; 78(1-3):199-209; and Bryant et al., "The effects of crosslinking density on cartilage formation in photocrosslinkable hydrogels", *Biomed Sci Instrum* 1999; 35:309-14; and Burdick et al., "Delivery of osteoinductive growth factors from degradable PEG hydrogels influences osteoblast differentiation and mineralization", *J Control Release* 2002; 83(1):53-63.) One of the challenges is the design and fabrication of the biodegradable scaffolds which are instructive for specific cellular functions and may thus regulate cell adhesion, proliferation, expression of a specific phenotype and extracellular matrix (ECM) deposition in a predictable and controlled fashion. (See, Genes et al., "Effect of substrate mechanics on chondrocyte adhesion to modified alginate surfaces", *Arch Biochem Biophys* 2004; 422(2):161-7; and Loty et al., "Phenotypic modulation of nasal septal chondrocytes by cytoskeleton modification", *Biorheology* 2000; 37(1-2):117-25; and Mahmood et al., "Adhesion-mediated signal transduction in human articular chondrocytes: the influence of biomaterial chemistry and tenascin", *C Exp Cell Res* 2004; 301 (2):179-88.) It is known that cell behavior on synthetic polymers is related to both the physical and chemical properties of the substrate. (See, Mahmood et al., "Adhesion-mediated signal transduction in human articular chondrocytes: the influence of biomaterial chemistry and tenascin", *C Exp Cell Res* 2004; 301 (2): 179-88; and Dadsetan et al., "Cell behavior on laser surface-modified polyethylene terephthalate in vitro", *J Biomed Mater Res* 2001; 57(2):183-9; and Dadsetan et al., "Surface chemistry mediates adhesive structure, cytoskeletal organization, and fusion of macrophages", *J Biomed Mater Res* 2004; 71A(3):439-48.) Scaffold physical properties may control cell function by regulating the diffusion of nutrients, waste products and cell-cell interactions, whereas scaffold surface chemistry affects cell adhesion, morphology and subsequent cellular activity by controlling protein adsorption. (See, Collier et al., "Protein adsorption on chemically modified surfaces", *Biomed Sci Instrum* 1997; 33:178-83; and Jones et al., "Macrophage behavior on surface-modified polyurethanes", *J Biomater Sci Polym Ed* 2004; 15(5):567-84.)

Cartilage cells are an ideal model for the study of cell-substrate interactions due to the tight relationships that have been established between chondrocytes morphology and function. (See, Miot et al., "Effects of scaffold composition and architecture on human nasal chondrocyte redifferentiation and cartilaginous matrix deposition", *Biomaterials* 2005; 26(15):2479-89.) This ability arises largely from the cartilage ECM, an abundant network of collagen, protoglycan and other molecules. The ECM interacts with chondrocytes through a variety of receptors to modulate chondrocyte metabolism phenotype and response to mechanical load. (See, Genes et al., "Effect of substrate mechanics on chondrocyte adhesion to modified alginate surfaces", *Arch Biochem Biophys* 2004; 422(2):161-7; and Sah et al., "Biosynthetic response of cartilage explants to dynamic compression", *J Orthop Res* 1989; 7(5):619-36.) Understanding how chondrocytes respond to specific, individual ECM signals would provide insights into the pathogenesis of diseases like osteoarthritis, which is known to be precipitated by mechanical factors. (See, Radin et al., "Effects of mechanical loading on the tissues of the rabbit knee", *J Orthop Res* 1984; 2(3):221-34; and Cooper et al., "Occupational activity and osteoarthritis of the knee", *Ann Rheum Dis* 1994; 53(2):90-3.)

In vitro chondrocyte culture on substrates in two dimensions has been shown to reduce gene expression and production of cartilage specific proteins such as collagen type II and aggrecan and quickly dedifferentiate to a more fibroblastic phenotype. (See, Loeser, "Integrin-mediated attachment of articular chondrocytes to extracellular matrix proteins", *Arthritis Rheum* 1993; 36(8):1103-10.) A number of researches have investigated techniques to reexpress the chondrogenic phenotype during chondrocyte expansion in monolayer culture by growing cells on microcarriers using growth factors, such as basic fibroblastic growth factors (bFGF-2) (See, Martin et al., "Enhanced cartilage tissue engineering by sequential exposure of chondrocytes to FGF-2 during 2D expansion and BMP-2 during 3D cultivation", *J Cell Biochem* 2001; 83(1):121-8), or incorporating cytoskeleton modifying drugs such as cytochalasin D. (See, Loty et al., "Cytochalasin D induces changes in cell shape and promotes in vitro chondrogenesis: a morphological study", *Biol Cell* 1995; 83(2-3):149-61.) However, the impact of material properties on the events that regulate cellular phenotype has not been extensively researched. (See, Mahmood et al., "Adhesion-mediated signal transduction in human articular chondrocytes: the influence of biomaterial chemistry and tenascin", *C Exp Cell Res* 2004; 301(2):179-88; and Papadaki et al., "The different behaviors of skeletal muscle cells and chondrocytes on PEGT/PBT block copolymers are related to the surface properties of the substrate", *J Biomed Mater Res* 2001; 54(1):47-58.)

A variety of materials have been suggested for the use in cartilage repairs. These materials have included natural polymers such as collagen, alginate and hyaluronic acid as well as synthetic polymers such as polyacrylamides, poly(vinyl alcohol) and poly(ethylene glycol) (PEG). (See, Yaylaoglu et al., "Development of a calcium phosphate-gelatin composite as a bone substitute and its use in drug release", *Biomaterials* 1999; 20(8):711-9; and Rowley et al., "Alginate hydrogels as synthetic extracellular matrix materials", Biomaterials 1999; 20(1):45-53; and Temenoff et al., "Injectable biodegradable materials for orthopedic tissue engineering", *Biomaterials* 2000; 21(23):2405-12; and Jasionowski et al., "Thermally-reversible gel for 3-D cell culture of chondrocytes", *J Mater Sci Mater Med* 2004; 15(5):575-82; and Noguchi et al., "Poly (vinyl alcohol) hydrogel as an artificial articular cartilage: evaluation of biocompatibility", *J Appl Biomater* 1991; 2(2): 101-7; and Cruise et al., "In vitro and in vivo performance of porcine islets encapsulated in interfacially photopolymerized poly(ethylene glycol) diacrylate membranes", *Cell Transplant* 1999; 8(3):293-306; and Wallace et al., "A tissue sealant based on reactive multifunctional polyethylene glycol", *J Biomed Mater Res* 2001; 58(5):545-55.)

Oligo (poly (ethylene glycol) fumarate) (OPF) is a macromer that has been developed and has been used for fabrication of hydrogels with a redox initiation system. It is reported that OPF hydrogels are biodegradable and their mechanical properties and degradation rates are controlled by the molecular weight of the PEG used in macromer formation. (See, Jo et al., "Modification of oligo(poly(ethylene glycol) fumarate) macromer with a GRGD peptide for the preparation of functionalized polymer networks", *Biomacromolecules* 2001; 2(1):255-61; and Temenoff et al., "Effect of poly(ethylene glycol) molecular weight on tensile and swelling properties of oligo(poly(ethylene glycol) fumarate) hydrogels for cartilage tissue engineering", *J Biomed Mater Res* 2002; 59(3):429-37; and U.S. Pat. No. 6,884,778; and U.S. Patent Application Publication No. 2002/0028189.)

Thus, there is still a need for photocrosslinkable, injectable, biodegradable hydrogels that can be injected as a fluid into a bodily defect and photocrosslinked in the defect, that may incorporate various therapeutic agents, e.g., cells and/or growth factors, and that may be implanted via minimally invasive arthroscopic techniques.

SUMMARY OF THE INVENTION

The present invention provides biodegradable hydrogels developed from an oligo(poly(ethylene glycol) fumarate) (OPF) macromer. An important characteristic of the OPF hydrogels is that they crosslink in a few minutes at room temperature using low power UV light and a cytocompatible photoinitiator. N-vinyl pyrrolidinone (NVP) can be used as a comonomer and accelerator for photocrosslinking. These hydrogels have a high degree of swelling in aqueous environments, and can maintain their structural integrity at water contents above 95%. Thus, they can be applied for cell encapsulation and support cell viability in constructs that are several millimeters thick, since the exchange of nutrients and wastes can occur over distances of this magnitude in water. Additionally, the synthetic matrix properties (e.g. crosslink density, water content, modulus, and surface tension) can be tailored to fit its end use.

In this study, we chose photopolymerization for crosslinking of OPF. Photocrosslinking provides advantages such as spatial and temporal control over conventional crosslinking. Initiation does not require elevated temperature and polymerization rate is sufficiently rapid under physiological condition for in vivo placement. It has been used particularly in the microencapsulations of islets, controlled release application, blood vessel adhesion and bone restoration. (See, Cruise et al., "A sensitivity study of the key parameters in the interfacial photopolymerization of poly(ethylene glycol) diacrylate upon porcine islets", *Biotechnol Bioeng* 1998 57(6):655-65; and Cruise et al., "Characterization of permeability and network structure of interfacially photopolymerized poly(ethylene glycol) diacrylate hydrogels", *Biomaterials* 1998; 19(14):1287-94; and Lu et al., "Photopolymerization of multilaminated poly(HEMA) hydrogels for controlled release", *J Control Release* 1999; 57(3):291-300; and Dumanian et al., "A new photopolymerizable blood vessel glue that seals human vessel anastomoses without augmenting thrombogenicity", *Plast Reconstr Surg* 1995; 95(5):901-7; and Muggli et al., "Crosslinked polyanhydrides for use in orthopedic applications: degradation behavior and mechanics", *J Biomed Mater Res* 1999; 46(2):271-8.)

In one example, we employed long wavelength UV source and Irgacure® 2959 radical photoinitiator which has been reported as cytocompatible for crosslinking of OPF. (See, Bryant et al., "Cytocompatibility of UV and visible light photoinitiating systems on cultured NIH/3T3 fibroblasts in vitro", *J Biomater Sci Polym Ed* 2000; 11(5):439-57.) N-vinyl pyrrolidinone (NVP) was used as co-monomer and accelerator for photocrosslinking. An accelerating role has been previously reported for NVP in photoencapsulation of pancreatic islets. (See, Cruise et al., "A sensitivity study of the key parameters in the interfacial photopolymerization of poly (ethylene glycol) diacrylate upon porcine islets", *Biotechnol Bioeng* 1998; 57(6):655-65.) We demonstrated that mechanical property, swelling behavior and degradation rates of hydrogels can be controlled by the change in NVP concentration. Moreover, we present data showing that changes in hydrogel properties affect adhesion, proliferation and morphology of the chondrocytes cultured on these hydrogels. Photoencapsulation of chondrocytes into OPF hydrogels was also investigated.

These and other features, aspects, and advantages of the present invention will become better understood upon consideration of the following detailed description, drawings, and appended claims.

DETAILED DESCRIPTION OF THE INVENTION

Figure 1A:
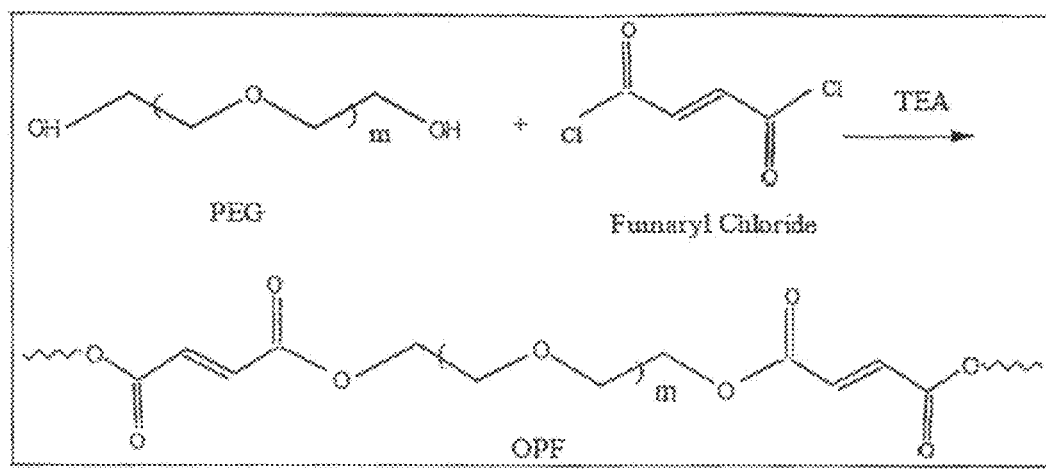
FIG. 1A shows the synthesis of oligo(poly(ethylene glycol) fumarate) (OPF) from polyethylene glycol and fumaryl chloride.

In one embodiment, the invention provides a photocrosslinkable, biodegradable material that may be used to form hydrogels. In one form, the material includes oligo(poly(ethylene glycol) fumarate), an unsaturated pyrrolidinone monomer, and a photoinitiator for photocrosslinking. The material is preferably injectable for in situ crosslinking in a patient's body by way of application of light. One or more bioactive agents may be included in the material. In one example, cells selected from the group consisting of chondrogenic cells and osteogenic cells are included in the material for cartilage growth and/or bone growth applications. The material may include a porogen, such as sodium chloride particles, for formation of a porous scaffold. In another form, the photocrosslinkable, biodegradable material includes oligo(poly(ethylene glycol) fumarate), cells selected from the group consisting of chondrogenic cells and osteogenic cells, and a photoinitiator. The invention also provides a method for tissue regeneration in which the material is injected into a patient's body, and the material is photocrosslinked by way of a light source to form a scaffold to allow for tissue regeneration.

In this embodiment, non-limiting example photoinitiators include 1-[4-(2-hydroxyethoxy)-phenyl]-2-hydroxy-2-methyl-1-propane-1-one, acetophenone, benzophenone, and the benzoin ethers. Preferably, the photoinitiators are cytocompatible. N-vinyl pyrrolidinone (NVP) can be used as a monomer and as an accelerator for photocrosslinking. Other non-limiting example accelerators include N,N dimethyl toluidine or tetramethyl-ethylenediamine. Preferably, the material photocrosslinks in the temperature range of 30° C. to 45° C. such that photocrosslinking at human body temperatures is possible. In one example form, a weight ratio of oligo(poly(ethylene glycol) fumarate) to pyrrolidinone monomer in the material is in the range of 1:0.01 to 1:0.5, and the material includes 20% to 240% by weight of the oligo(poly(ethylene glycol) fumarate).

In another embodiment, the invention provides a biodegradable hydrogel prepared by photocrosslinking oligo(poly(ethylene glycol) fumarate) and an unsaturated pyrrolidinone monomer. The hydrogel can include 95 weight percent or more water and retain structural integrity. The hydrogel may include one or more bioactive agents. The hydrogel may be photocrosslinked in an aqueous solution. Preferably, a weight ratio of oligo(poly(ethylene glycol) fumarate) to pyrrolidinone monomer before photocrosslinking is in the range of 1:0.01 to 1:0.5.

In yet another embodiment, the invention provides a scaffold for tissue regeneration. The scaffold includes a biodegradable matrix including (i) a hydrogel prepared by photocrosslinking oligo(poly(ethylene glycol) fumarate), and (ii)

cells selected from the group consisting of chondrogenic cells and osteogenic cells. The hydrogel may be prepared by photocrosslinking oligo(poly(ethylene glycol) fumarate) and an unsaturated pyrrolidinone monomer. The cells may be encapsulated in the matrix, and/or the cells may be adhered to a surface of the matrix. The cells may have a spherical morphology, and/or the cells may have a flattened morphology. The cells may be suspended in collagen or a collagen derivative such as gelatin or atelocollagen. The scaffold may be porous, and the hydrogel may prepared by photocrosslinking oligo(poly(ethylene glycol) fumarate) in the presence of a porogen. Preferably, the scaffold has a porosity of 70% to 90%. The invention also provides a method for tissue regeneration in which the scaffold is implanted into a patient's body to allow for tissue regeneration.

In certain non-limiting example versions of the invention, oligo(poly(ethylene glycol) fumarate) (OPF), a biocompatible and biodegradable macromer was used for fabrication of OPF hydrogels. OPF was crosslinked using UV light, photoinitiator and N-vinylpyrolidinone (NVP) as co-monomer and crosslinking agent. We demonstrated that hydrogel crosslinking levels could be controlled by the change in NVP concentration in initial macromer solution. The effect of crosslinking levels was then studied on swelling behavior, mechanical properties and degradation rates of hydrogels. Our results showed that equilibrium swelling of hydrogels decreased with the increase in crosslinking density while compression modulus increased. We also demonstrated that hydrogels degradation rate was correlated with the crosslinking levels of hydrogels. Hydrogel degradation rate decreased as crosslinking levels increased. In order to examine the effect of hydrogel surface property on cell adhesion and morphology, chondrocytes were cultured on the surface of hydrogels with varying crosslinking levels. The change in crosslinking levels appeared to modulate chondrocyte attachment and morphology on the OPF hydrogels. Furthermore, viability of the photoencapsulated chondrocytes into the OPF hydrogels was examined. Cell viability appeared to remain high after 21 days.

As used herein, a "biodegradable" material is one which decomposes under normal in vivo physiological conditions into components which can be metabolized or excreted. By "injectable", we mean the material may be delivered to a site by way of a medical syringe or an arthroscopic device. By "photocrosslinkable", we mean the functional groups of a polymer may crosslink with the functional groups of the same polymer or another monomer or polymer by application of photons (e.g., UV light) in the presence of a photoinitiator.

The term "molecular weight" in this specification refers to "weight average molecular weight" ($M_w = \Sigma_i N_i M_i^2 / \Sigma_i N_i M_i$). Although weight average molecular weight ($M_w$) can be determined in a variety of ways, with some differences in result depending upon the method employed, it is convenient to employ gel permeation chromatography. As used herein, the term "number average molecular weight" ($M_n$) refers to the total weight of all the molecules in a polymer sample divided by the total number of moles present ($M_n = \Sigma_i N_i M_i / \Sigma_i N_i$). Although number average molecular weight can be determined in a variety of ways, with some differences in result depending upon the method employed, it is convenient to employ gel permeation chromatography.

A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, enzymes, organic catalysts, ribozymes, organometallics, proteins, glycoproteins, peptides, polyamino acids, antibodies, nucleic acids, steroidal molecules, antibiotics, antimycotics, cytokines, growth factors, carbohydrates, oleophobics, lipids, extracellular matrix and/or its individual components, pharmaceuticals, and therapeutics.

EXAMPLES

The following Examples have been presented in order to further illustrate the invention and are not intended to limit the invention in any way.

In the Examples, statistical analysis was performed using the StatView version 5.0.1.0 (SAS Institute Inc. Cary, N.C.) using Post Hoc ANOVA (Bonfferoni/Dunn) with a significance levels of $p<0.05$.

A. Macromer Synthesis

Oligo(poly(ethylene glycol) fumarate) (OPF) was synthesized using polyethylene glycol (PEG) (available from Aldrich) with the initial molecular weight of 10 kDa according to a method published at Jo et al., "Modification of oligo(poly (ethylene glycol) fumarate) macromer with a GRGD peptide for the preparation of functionalized polymer networks", *Biomacromolecules* 2001; 2(1):255-61. See, also FIG. 1A. Briefly, 50 g PEG was azeotropically distilled in toluene to remove residual water and then dissolved in 500 milliliters distilled methylene chloride. The resulting PEG was placed in the ice bath and purged with nitrogen for 10 minutes, then 0.9 mole triethylamine (TEA, Aldrich) per mole PEG and 1.8 mole distilled fumaryl chloride (Acros) per mole PEG was added dropwise. The reaction was maintained in a nitrogen environment. The reaction vessel was then removed from the ice bath and stirred at room temperature for 48 hours. For purification, methylene chloride was removed by a rotary evaporator. The resulting OPF was dissolved in ethyl acetate and filtered to remove the salt from the reaction of TEA and chloride. The OPF was recrystallized in ethyl acetate and vacuum dried over night.

B. Molecular Weight of Macromer

The molecular weights of OPF macromer and PEG used for synthesis were measured by a Waters 717 Plus Autosampler GPC system connected to a model 515 HPLC pump and model 2410 refractor index detector. After dissolution in tetrahydrofuran, 20 μl of polymer solutions at the concentration of 20 mg/ml were injected into the columns consisted of styragel HT guard column (7.8×300 mm, Waters) in series with a styragel HR 4E column (7.8×300 mm, Waters) at a flow rate of 1 ml/min. Monodispersed polystyrene standards (Polysciences, Warrington, Pa.) with Mn of 0.474, 6.69, 18.6 and 38 KDa and polydispersities of less than 1.1 were used for the calibration curve. Three samples of each material were analyzed.

GPC analysis indicated that synthesized OPF had a number average molecular weight ($M_n$) of 9727±1966 and a weight average molecular weight ($M_w$) of 16246±3710, while the PEG used for production of this OPF macromer had $M_n$ of 9154±466 and $M_w$ of 11465±407.

C. Hydrogel Fabrication

Hydrogels were made by dissolving the OPF macromer with a final concentration of 33% and 25% (w/w) in deionized water containing 0.05% (w/w) Irgacure® 2959 radical photoinitiator (available from Ciba-Specialty Chemicals) and N-vinyl pyrrolidinone (NVP) as a comonomer and accelerator for photocrosslinking with different concentrations (see Table 1). The product sheet for Irgacure® 2959 describes Irgacure® 2959 as being 1-[4-(2-Hydroxyethoxy)-phenyl]-2-hydroxy-2-methyl-1-propane-1-one and as having the following structure:

TABLE 1

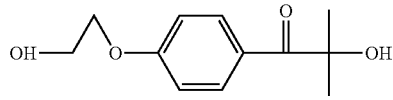 [SMILES: CC(C)(O)C(=O)c1ccc(OCCO)cc1]

| Description of OPF Hydrogels | |
|---|---|
| Hydrogels | OPF: NVP Ratio (w/w) |
| N5 | 1:0.05 |
| N10 | 1:0.1 |
| N20 | 1:0.2 |
| N30 | 1:0.3 |

Figure 1B:
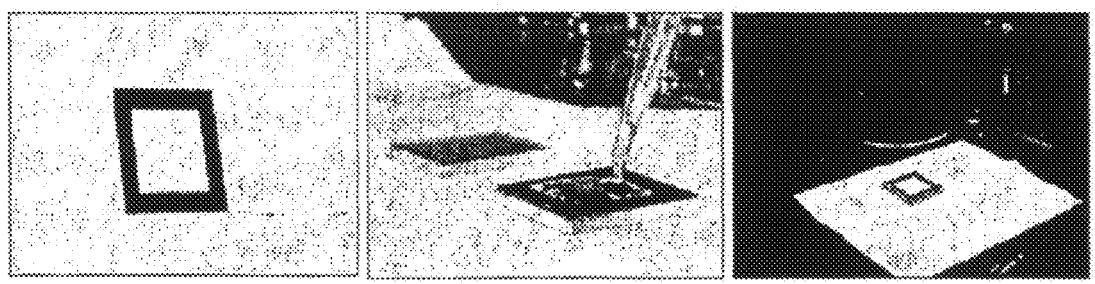
FIG. 1B shows OPF macromer injection into a mold and UV crosslinking.
Figure 2:
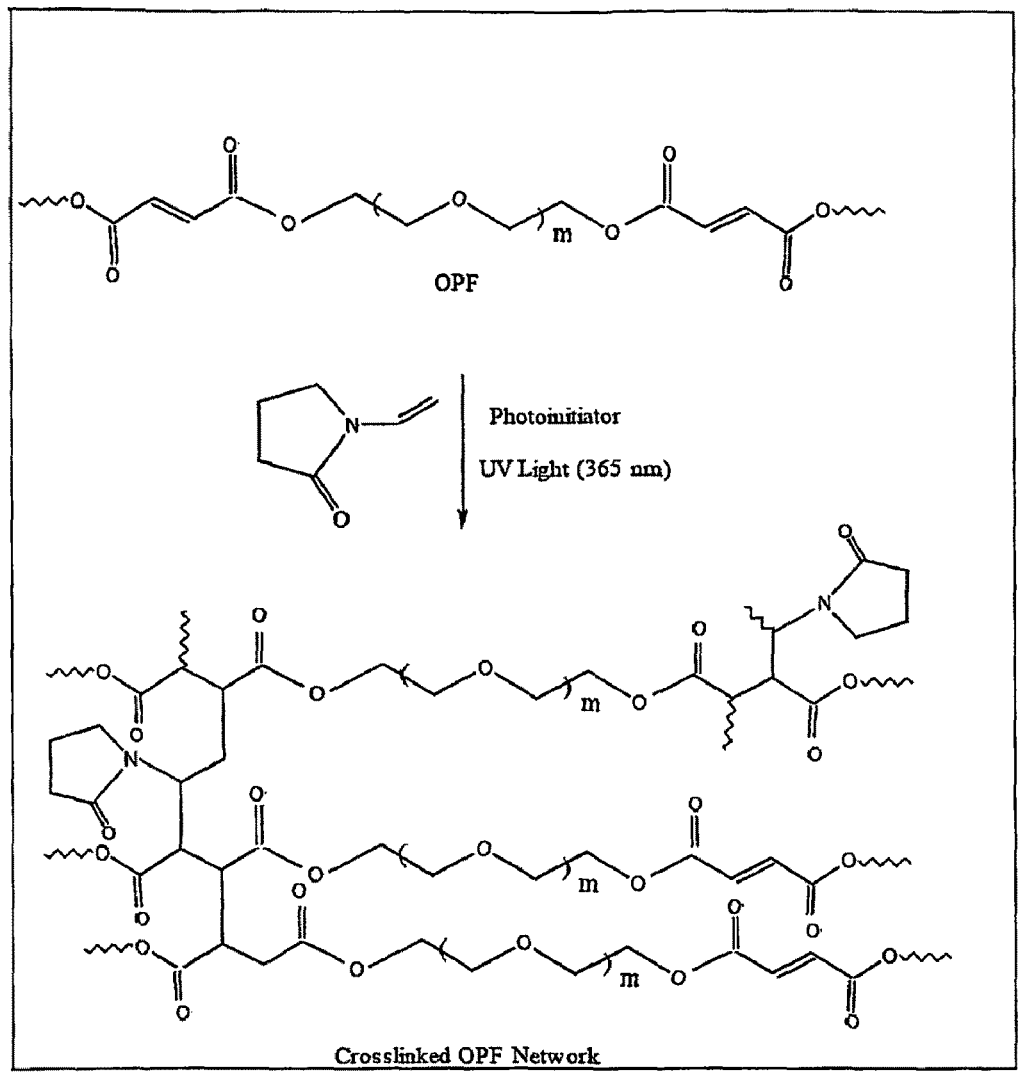
FIG. 2 shows a schematic of a photocrosslinking reaction for the fabrication of oligo(poly(ethylene glycol) fumarate) (OPF) hydrogels.

The macromer solution was pipetted between glass slides with a 1 mm spacer and polymerized using 365 nm UV light at the intensity of ~8 mW/cm$^2$ (Blak-Ray Model 100AP) for 10 minutes. See FIGS. 1B and 2.

D. Chemical Characterization of OPF Hydrogel

The crosslinked OPF hydrogel was characterized using FT-IR and NMR. FT-IR of the crosslinked OPF films was acquired by a Nicolet 550 spectrometer after drying in reduced pressure and after equilibrium swelling in distilled water. $^{13}$C nuclear magnetic resonance (NMR) spectra of OPF macromer was acquired on a Varian Mercury Plus spectrometer ($^{13}$C=100.6 MHz) using CDCl$_3$ solutions containing TMS. Solid-state $^{13}$CNMR spectra of photocrosslinked hydrogels were obtained using a Varian Inova spectrometer (600 MHZ) after drying the samples.

Figure 3:
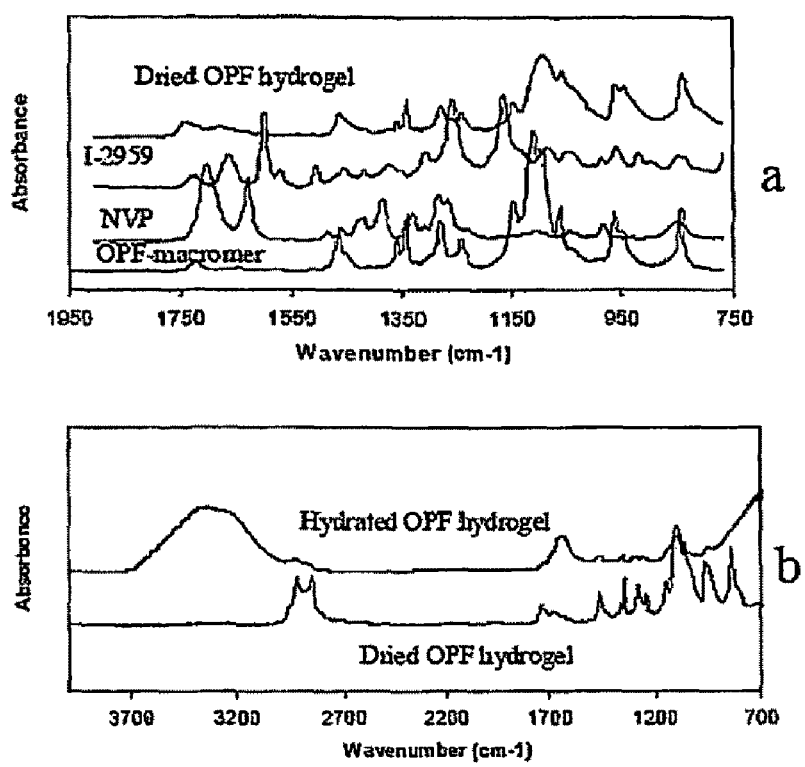
FIG. 3 shows in (a) an FT-IR spectra of OPF 10 K, NVP, I-2959 photoinitiator and OPF hydrogel after crosslinking and drying, and in (b) hydrated hydrogel versus the dried one. FT-IR means Fourier Transform Infrared Spectroscopy herein.

FIG. 3 shows FT-IR spectra of the starting materials the for fabrication of OPF hydrogel as well as the spectra of the photocrosslinked OPF hydrogel at the both hydrated and dried states. The small band seen at about 1600 cm$^{-1}$ in OPF macromer spectra corresponds to fumarate double bond, which is further involved in OPF photocrosslinking. The —C=O stretching band of fumarate group is also seen at 1724 cm$^{-1}$ (FIG. 3a). In FIG. 3b, the —C=O stretching of NVP appears at about 1770 cm$^{-1}$ together with the —C=O stretching of the fumarate group in dried hydrogel. However, with the hydration of hydrogel, peaks at 1724 cm$^{-1}$ and 1770 cm$^{-1}$ merge together and appear as a single broad band. The broad band seen at about 3500 cm$^{-1}$ is indicative of hydrogel hydration and swelling.

Figure 4:
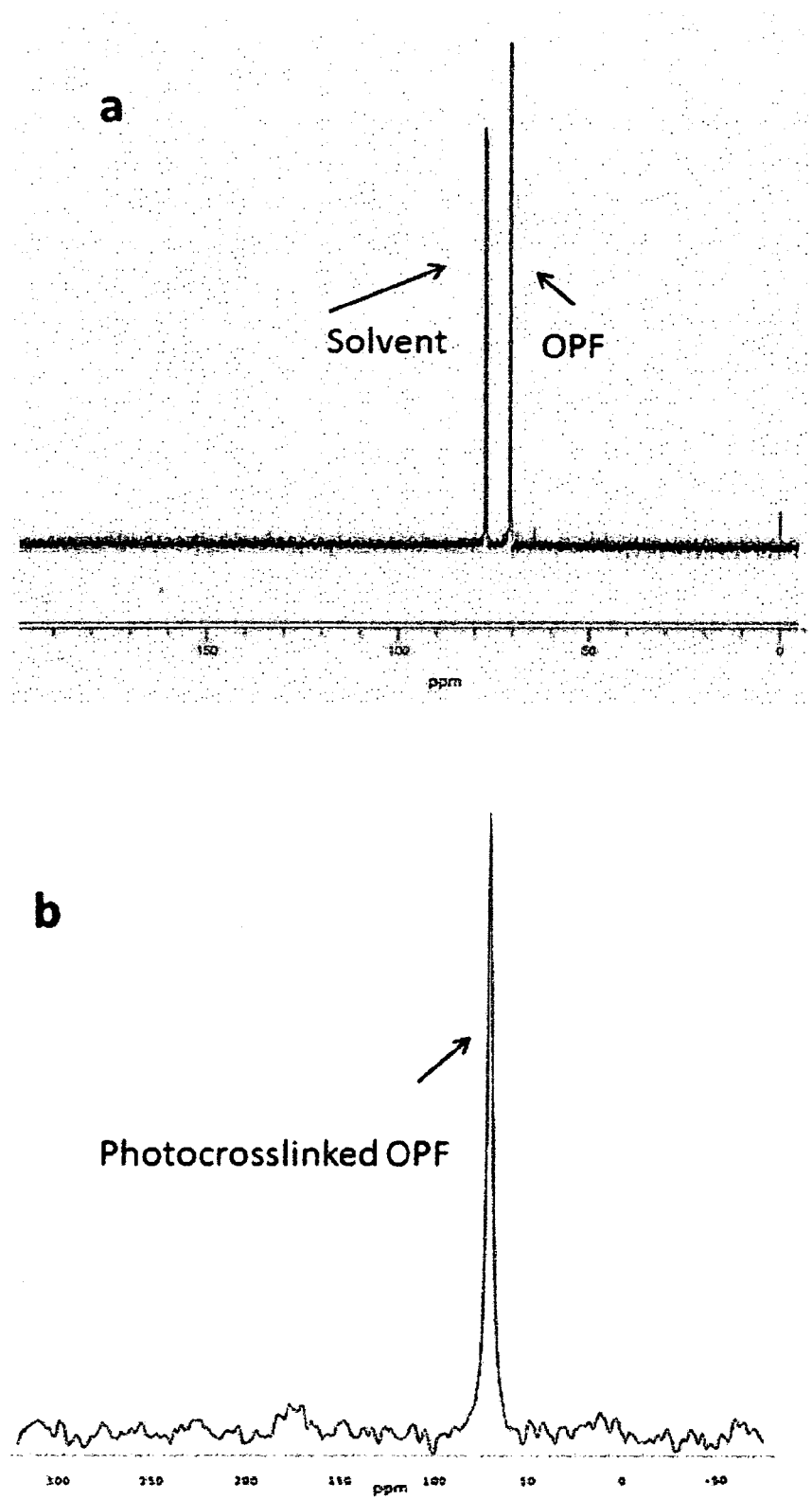
FIG. 4 shows in (a) $^{13}$C-NMR of OPF before crosslinking in solvent, and in (b) solid state $^{13}$C-NMR of OPF after photocrosslinking and drying. NMR means Nuclear Magnetic Resonance Spectroscopy herein.

FIG. 4 shows $^{13}$CNMR of OPF before and after crosslinking. The major chemical shift for OPF macromer is seen at 70.4 ppm corresponding to PEG methylene groups. Similar peak appears at about 70.4 ppm in solid state $^{13}$CNMR of OPF after photocrosslinking.

E. Hydrogel Characterization

1. Compression Testing

After crosslinking, hydrogels were cut into disks of 10 mm. diameter with a cork borer and swollen in phosphate buffered saline (PBS) for 24 hours. Compressive modulus of the various swollen hydrogels was determined using a dynamic mechanical analyzer (DMA-2980, TA Instruments) at a rate of 4 N/min. The modulus was determined as the slope of the stress versus strain curve at low strains (<20%).

Figure 5:
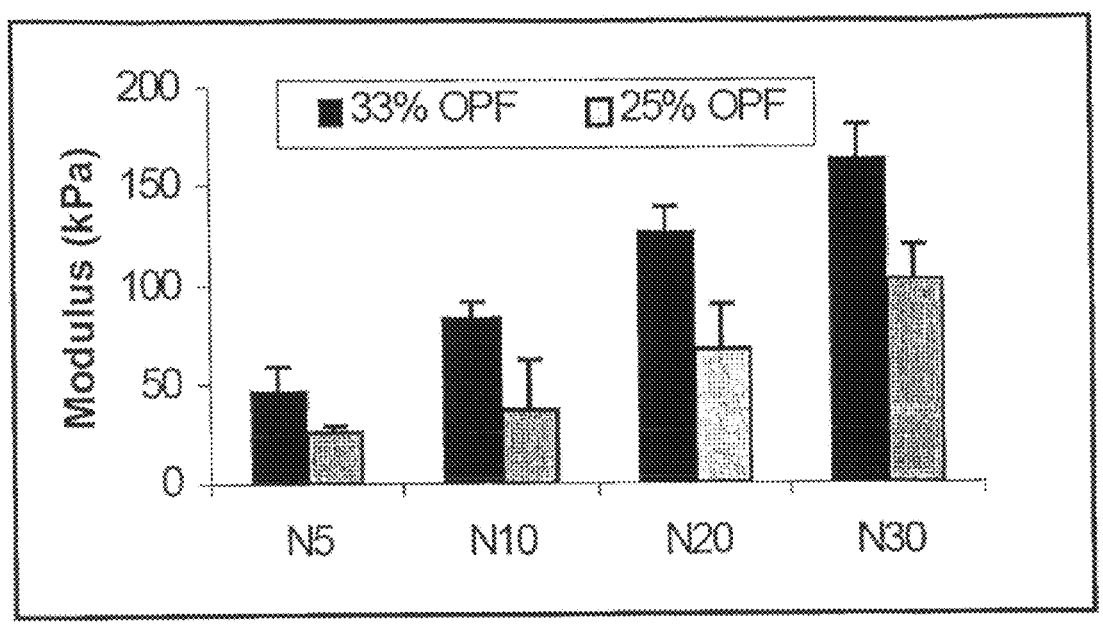
FIG. 5 shows the compression modulus of various OPF hydrogels.

FIG. 5 shows that compressive modulus of OPF hydrogels increased with the increase in concentration of NVP in precursor solutions ranging from 25 to 102 kPa for the hydrogels fabricated from 25% wt macromer. An increase in macromer concentration from 25% wt to 33% wt led to a statistically significant increase in modulus of the hydrogels. For instance, N30 fabricated from 25% wt macromer had a modulus of 102 kPa, but increased to 163 kPa when the macromer concentration increased to 33% wt. Overall, increase in modulus was correlated to the increase in hydrogel crosslinking density.

2. Swelling Behavior

Figure 6:
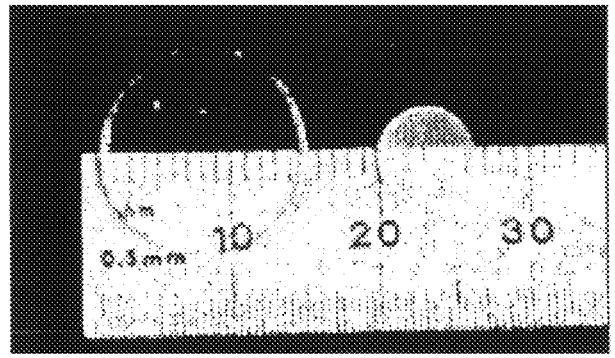
FIG. 6 shows an OPF hydrogel before (right) and after swelling (left).

Ten millimeter disks of OPF hydrogels were prepared as mentioned above and swollen in PBS to equilibrium swelling (24 hours) at 37° C. See FIG. 6.

Swollen samples were blotted dry and weighed (Ws), and then dried in reduced pressure and weighed again (Wd). The swelling ratio of the hydrogels was calculated using the following equation: Swelling ratio=(Ws−Wd)/Wd.

Theoretical sol fraction was calculated for various hydrogels using following equation where k represents the approximate weight fraction of polymer in the solution prior to crosslinking, k=0.33. Experiments were conducted with n=3 for both the swelling and sol fraction measurements. Sol fraction=(k Wi−Wd)/k Wi.

Figure 7:
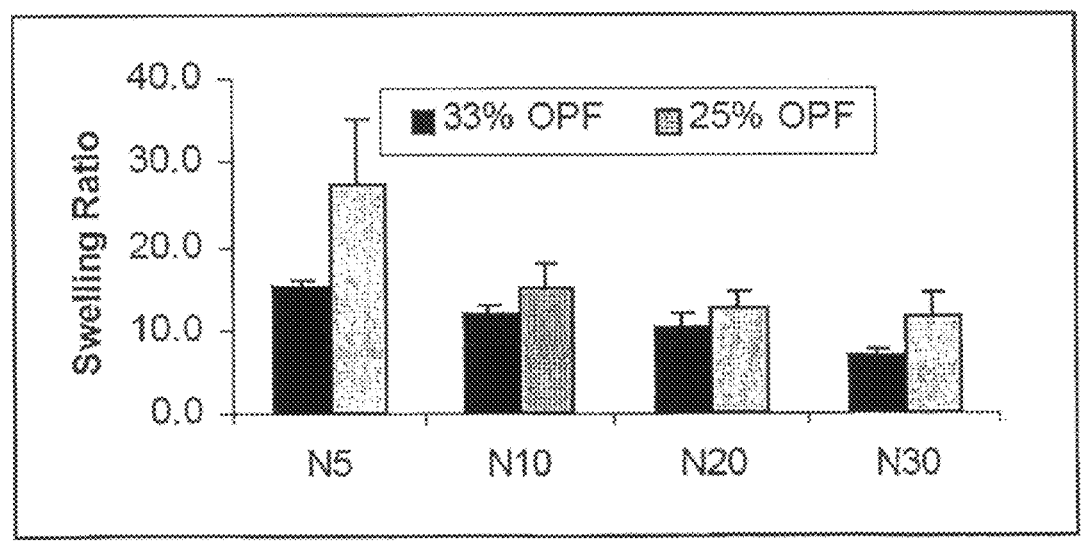
FIG. 7 shows the equilibrium swelling of OPF hydrogels with different crosslinking levels. Hydrogels with lower concentrations of macromer and crosslinker had a higher swelling ratio.

The equilibrium swelling ratios of the various OPF hydrogels are shown in FIG. 7. A decreasing trend was seen for swelling ratios of the hydrogels with increasing NVP concentration in initial macromer solution indicating an accelerating role for NVP as crosslinking agent. Variations in equilibrium swelling ratios were in the range of ~27 to 11 for the hydrogels fabricated from 25% wt OPF macromer with varying NVP concentrations. FIG. 7 shows that swelling ratios of hydrogels decreased when macromer concentration increased from 25% to 33% as expected. This decrease in swelling ratio was statistically significant for N5 and N10 (p<0.05), whereas differences in swelling ratios of hydrogels with higher NVP levels were not significant.

3. In Vitro Degradation

Disks of hydrogels were placed into the wells of 12 well tissue culture plates containing 2.5 milliliters of PBS and incubated at 37° C. on an orbital shaker. The PBS was replaced every other day for the first week and then weekly thereafter. The swelling ratio of the hydrogels were measured at days 7, 14 and 21 as described above.

Figure 8:
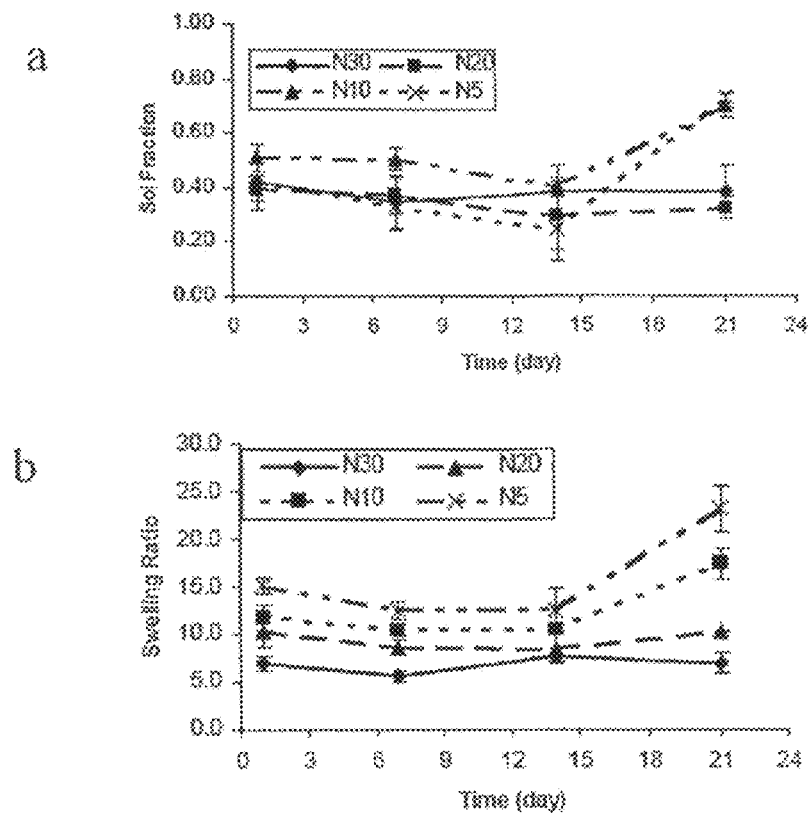
FIG. 8 shows the degradation behavior for crosslinked OPF hydrogels. Swelling ratio (a) and sol fraction (b) of OPF hydrogels in PBS over 21 days at 37° C. Hydrogels with lower crosslinking levels (N5 and N10) began to degrade after 14. Data represent mean±STD, (n=3).

Results from degradation study in PBS showed that swelling ratio for hydrogels with lower crosslinking levels (N5 and N10) was constant up to 14 days and then increased dramatically to 23.3 and 17.5 for N5 and N10, respectively at day 21 (FIG. 8a). This increase in swelling ratio indicated that hydrogel network began to degrade after two weeks. However, swelling ratio of N20 and N30 remained constant after 21 days indicating a lower degradation rate for the hydrogels with higher crosslinking levels. Sol fractions of OPF hydrogels in PBS over time are shown in FIG. 8b. Likewise swelling ratio, sol fraction of hydrogels remained constant until day 14 and then significantly increased at day 21 for N5 and N10 samples, whereas there was no difference in sol fraction of N20 and N30 hydrogels over time. To accelerate the degradation rate of hydrogels, additional experiments were performed in 1M KOH. Weight loss data showed 100% degradation for N5 and N10 after 10 days, whereas only 85% of N30 was degraded at the same time period. It appears there is a good correlation between degradation time and hydrogel crosslinking density.

4. Cell Adhesion and Morphology on OPF Hydrogels: For Application in Guided Tissue Regeneration ATDC cells (RIKEN Cell Bank, Tsukuba, Ibaraki, Japan), a clonal mouse chondrogenic cell line, were grown to confluence in standard culture flasks in a 1:1 mixture of Dulbecco's Modified Eagle's Medium (DMEM) (Gibco BRL, Rockville, N.Y., USA) and Ham's F12 medium (Nissui Pharmaceutical, Japan), supplemented with 5% Fetal Bovine Serum (Invitrogen), 10 μg/ml Human transferrin (Roche) and $3 \times 10^{-8}$ M sodium selnite (Sigma). Cells were maintained in a humidified atmosphere of 5% $CO_2$. Culture medium was changed every 2 days. The cells were then trypsinized and used in adhesion experiments.

Swollen hydrogel disks were disinfected with 70% ethanol, and washed several times with PBS. Hydrogel films were placed into the 24-well tissue culture plates, secured with sterile silicone rubber rings (Cole-Parmer, Vernon Hills, Ill.) and incubated in DMEM media 24 h prior to cell culture. Suspended chondrocytes were seeded onto the hydrogels at the concentration of $2 \times 10^4$ cells/$cm^2$ and incubated at 37° C. After 4 hours, media was removed and plates were rinsed with warmed PBS to remove non adherent cells and 1 milliliter of fresh media was added. Media was replaced every 2-3 days. At desired time points, total number of adherent cells was counted manually from five 20x-objective fields (0.208 $mm^2$) viewed by optical microscope (OM) and averaged to determine the cell densities as previously described at Jones et al., "Macrophage behavior on surface-modified polyurethanes", *J Biomater Sci Polym Ed* 2004; 15(5):567-84. Duplicates of two individual experiments were analyzed for cell densities. The morphology of attached cells was visualized by phase contrast microscopy (Axiovert 25, Carl Zeiss, Inc. Thornwood, N.Y.) equipped by a CCD camera. Polystyrene tissue culture plates were used as control.

ATDC cells were photoencapsulated in various hydrogel networks ($15 \times 10^6$ cells/ml) by suspension in the desired macromer solution, pipetting into a sterile mold with 1 millimeter spacers, and polymerization as described above. The resulting hydrogel-cell constructs were cut into disks of 5 millimeter diameter, covered with 2.5 milliliters culture media in a 12-well tissue culture plate and incubated in a humid environment with 5% $CO_2$. To determine the viability of the cells after encapsulation, the Live/Dead Viability/Cytotoxicity Kit (Molecular Probes, L3224) was used per kit instructions. This technique stains living cells green and dead cells red. After staining, the cells were visualized using confocal scanning microscopy.

Figure 16:
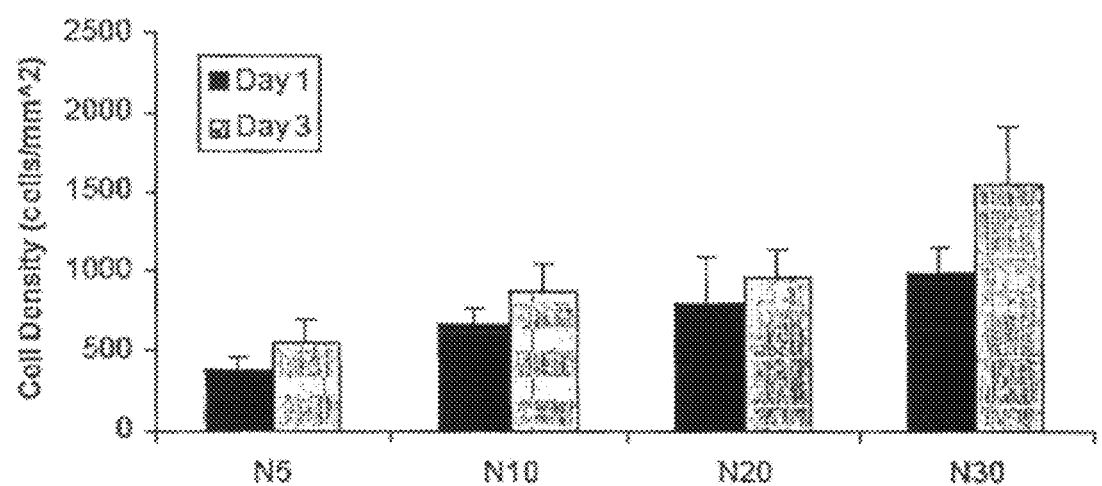
FIG. 16 shows cell density on OPF hydrogels after 1 and 3 days culture. Data represent mean±STD, (n=3).

Cell attachment: FIG. 16 shows ATDC cell densities on the OPF with varying crosslinking levels at days 1 and 3 of culture. As seen in this figure, cell attachments were dependent on crosslinking levels and increased with increasing NVP crosslinker concentration. Trend for cell density on OPF hydrogels at day 1 is as follows: N5 (389±72)<N10 (662±100)<N20 (795±301)<N30 (991±160)<tissue culture polystyrene (TCPS) (1178±185). At day 3, cell attachments on all hydrogels were slightly higher than those after 1 day; however differences were not statistically significant.

Figure 9:
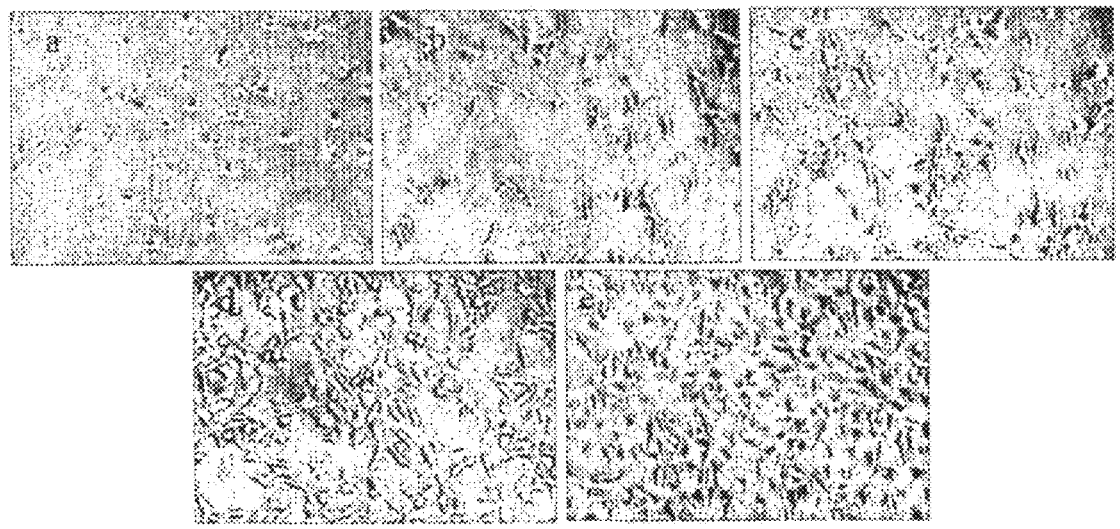
FIG. 9 shows chondrocyte adhesion and spreading on OPF hydrogels after 3 days: N5 (a), N10 (b), N20 (c), N30 (d) and TCPS (e). Surfaces with higher crosslinking density support more cell adhesion and spreading.

FIG. 9 indicates that adherent chondrocytes exhibited different morphologies on the surfaces with varying crosslinking levels. Cells on N5 hydrogel had spherical morphology, while they were spread and flattened on samples with increased crosslinking levels. Predominant cell morphology on the N20 and N30 surfaces was a large, flattened cell with stretched fibers which resembled those on TCPS.

5. Cell Encapsulation: For Cell Delivery

Figure 10:
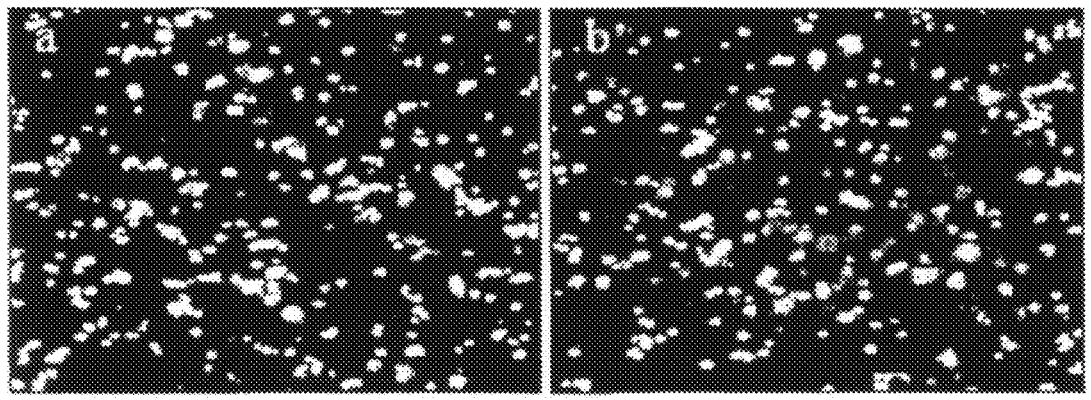
FIG. 10 shows the viability of rat marrow stromal cells in OPF hydrogels with different formulations (a) N5 and (b) N10 after 21 days. Live cells were stained green (which shows up as light areas in FIG. 10) and dead cells are stained red. All magnifications are ×10.
Figure 11:
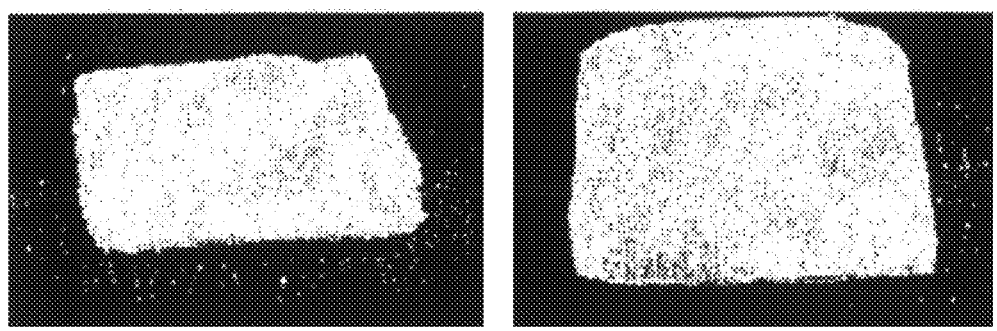
FIG. 11 shows the fabrication of a hydrogel sponge with a particulate leaching method for cell transplantation.

In order to determine the suitability of the hydrogels for cell delivery, rat marrow stromal cells and mouse chondrocytes (ATDC-5) were encapsulated into the gels and their viability was examined. ATDC cells were seeded within N5 and N10 hydrogels fabricated from 33% wt macromer and examined following 0, 1, 3, 7 and 21 days in culture to determine whether cells survive the photopolymerization process and remain viable during culture in these materials. Viable cells (>95%) were observed throughout the hydrogels at all times during 21 days culture period (FIG. 10). In addition, no differences in viability were noted across the thickness of the hydrogels scaffold at any time point in the culture period. See FIG. 10 where live cells were stained green (which shows up as light areas in FIG. 10).

F. Porous OPF Hydrogel for Cell Delivery to Bone Defects

Porous hydrogel provides adequate structure and surface area to implant a large volume of cells into the body to replace lost function organs. Marrow stromal cells (MSCs) (bone-growing cells) can be used in the invention to fill bone defects or to prepare entire new bones. Porous OPF hydrogel can be cut into a desired shape and size and delivered to the bone defect through a catheter and will re-expand when properly positioned in the defect. If necessary, adhesives can be used to adhere the sponge to the bone within the bone defect. Thereafter, MSCs are suspended in collagen and injected into the sponge. Collagen then solidifies and maintains the cells, which subsequently grow bone tissue and fill in the bone defect.

1. Fabrication Method

Porous hydrogel (sponge) was made using NaCl as porogen. Briefly, OPF macromer was diluted to a final concentration of 33% (w/w) in deionized water containing 0.05% (w/w) of a photoinitiator (Irgacure 2959, Ciba-Specialty Chemicals) and 0.33% (w/w) N-vinyl pyrrolidinone (NVP). In order to obtain hydrogels with 75%, 80% and 85% porosity, 1 milliliter of the macromer solution was mixed with 3, 4 and 5.7 grams of sodium chloride particles (100 to 500 μm diameter), respectively and polymerized using 365 nm UV light at an intensity of ~8 $mW/cm^2$ (Blak-Ray) for 10 minutes. The salt was leached out of the photocrosslinked polymer with soaking it in $dH_2O$ for 48 hours with three changes.

2. Morphology of Hydrogel Sponge

Figure 12:
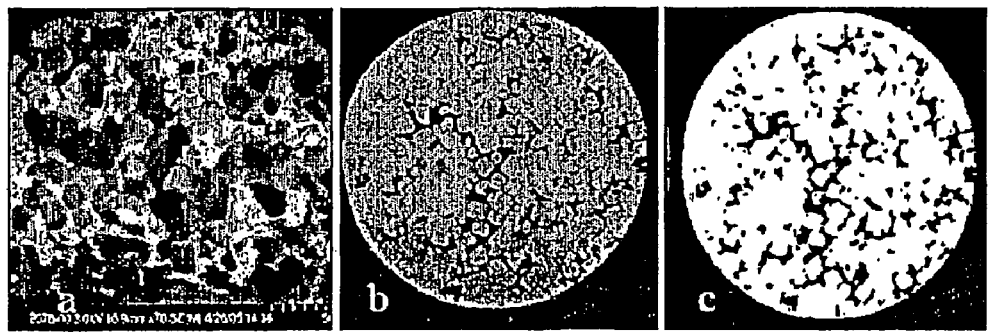
FIG. 12 shows in (a) a scanning electron microscope (SEM) of a hydrogel cross-section, in (b) a Micro-MR section, and in (c) a pore-solid delineation of OPF hydrogels with 75% salt porogen concentration of 100 μm diameter salt particles.
Figure 13:
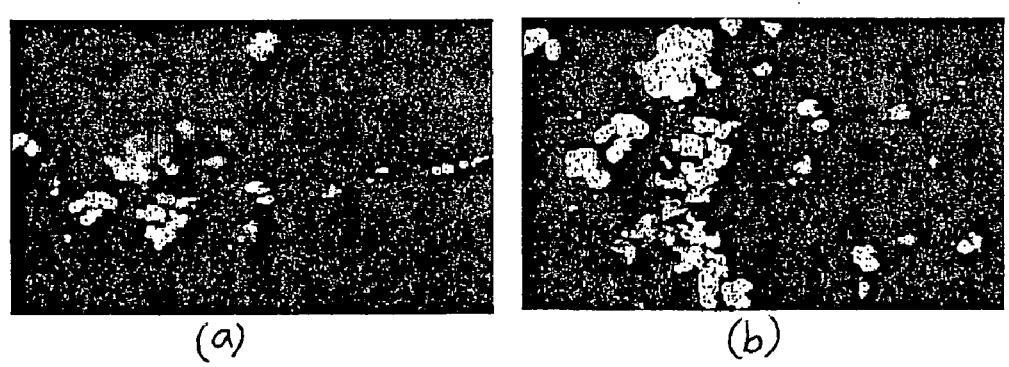
FIG. 13 shows in (a) a representative confocal microscope image of seeded cells after 7 days wherein cells are stained with live/dead kit and viable cells are stained green, and in (b) stack images of z sections taken with confocal microscope wherein cells are artificially colored by PhotoShop® to show the cells in different levels.

FIG. 12a shows an SEM image of a porous hydrogel with 75% porogen fraction. This picture reveals that the pores are highly interconnected. FIGS. 12b and 12c show a representative micro-MR cross-section and the corresponding pore-solid delineation of this scaffold in its swollen state. MR image analysis showed that the pores were highly interconnected and that the porosity computed from the images correlated well with the experimental porogen concentration.

3. Marrow Stromal Cell (MSC) Isolation and Culture

MSCs were isolated from the femurs and tibiae of male Sprague Dawely rats according to a previously described method. (See, Maniatopoulos, et al., "Bone formation in vitro by stromal cells obtained from bone marrow of young adult rats", *Cell Tissue Res.* 1988; 254:317-330.) Prior to cell seeding, samples were disinfected with 70% ethanol for 30 minutes. The ethanol was then aspirated, and the samples were soaked in sterile PBS for 1 hour with three changes, followed by two additional changes of media and incubation over night. A 25 μl sample of the cell suspension containing 225,000 cells was seeded onto the top of the hydrogel foams in 24 well plates and incubated for 3 hours to allow the cells to attach. Then 1 milliliter of osteogenic media was added to each well, and the medium was changed every 2-3 days. At days 1, 4, and 14, samples were washed with PBS three times and frozen in one milliliter $dH_2O$ at $-80°$ C. Samples underwent two freeze/thaw cycles with sonication on ice for 30 minutes after each cycle prior to analysis. Cell numbers were determined by the PicoGreen DNA kit (Molecular probes, Eugene, Oreg.) according to the manufacturer's instructions.

Alkaline phosphatase activity was measured using a commercially available kit, according to the manufacturer's instructions (Sigma Chemical).

Figure 14:
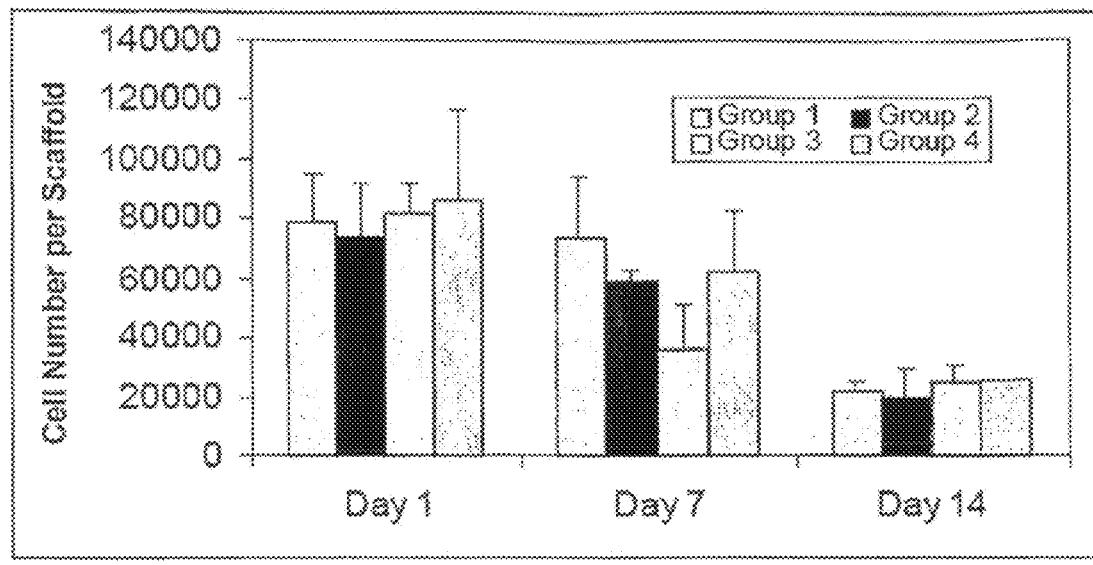
FIG. 14 shows the cell attachment to hydrogel sponges with different porosity.
Figure 15:
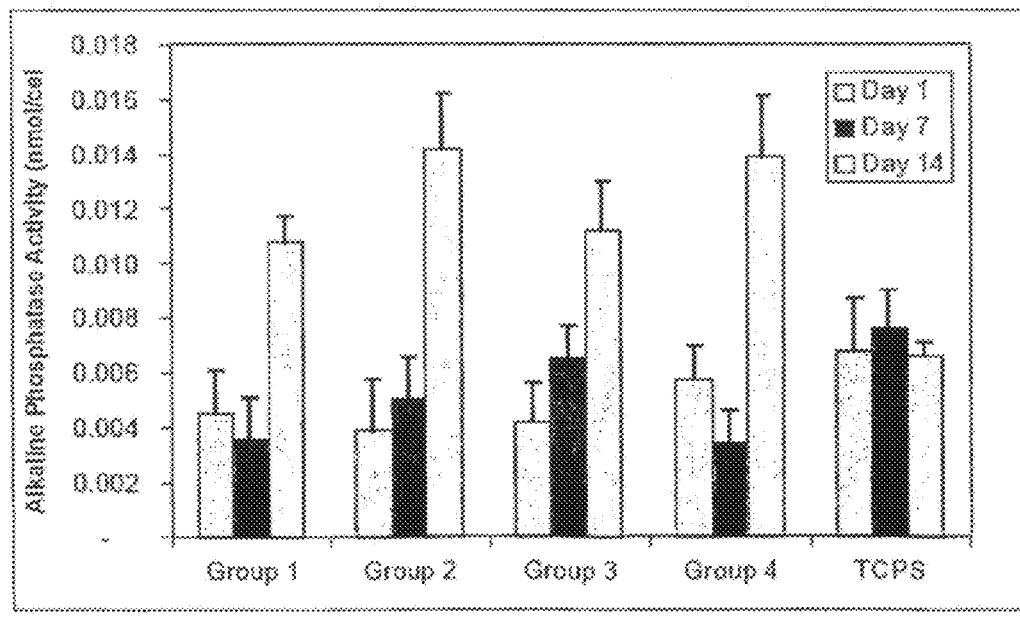
FIG. 15 shows the alkaline phosphatase (ALP) activity of the marrow stromal cells on porous scaffolds.

The total number of cells cultured on the porous hydrogels was quantified with a DNA assay; Cells did not show significant proliferation over a time period of 14 days and similar cell numbers were observed on the scaffolds at different time points (FIG. 14). Alkaline phosphatase (ALP) activity, an indicator of the osteoprogenitor cell's commitment to the osteoblastic phenotype, was measured and normalized by the total cell number for each sample. Results showed that the ALP activity of the cell-hydrogel composites was significantly higher than that of cells on tissue culture polystyrene (FIG. 15). This indicates that the porous hydrogel scaffolds supported differentiation of the MSCs to the osteoblastic phenotype.

G. In Vitro Cytotoxicity of the Leachable Components from OPF Hydrogels

OPF hydrogels were crosslinked as previously described in materials and methods. After crosslinking hydrogels were cut into the disks of 10 mm diameter and disinfected with 70% ethanol followed by three washes with sterile PBS. After disinfecting, hydrogel disks were placed in marrow stromal cell (MSC) media and incubated for 48 hours. The volume of media used to extract leachable products from OPF hydrogels was determined according to ISO/EN 10935 guidelines (e.g. 1 mL of media/3 $cm^2$ specimens). Concurrently, MSCs were seeded in 96-well plates and 20,000 cell/$cm^2$ cultured for 24 hours as previously described. After being leached for 24 hours, the OPF extract media was used with dilution of 10% and 100% and attached MSCs were exposed to all extract concentrations. Cell viability (metabolic activity was analyzed using MTS assay following manufacturer's guideline (Promega). Relative survival of each treatment was calculated as absorbance of each sample divided by the absorbance of the controls at the wavelength of 490 nm.

Figure 17:
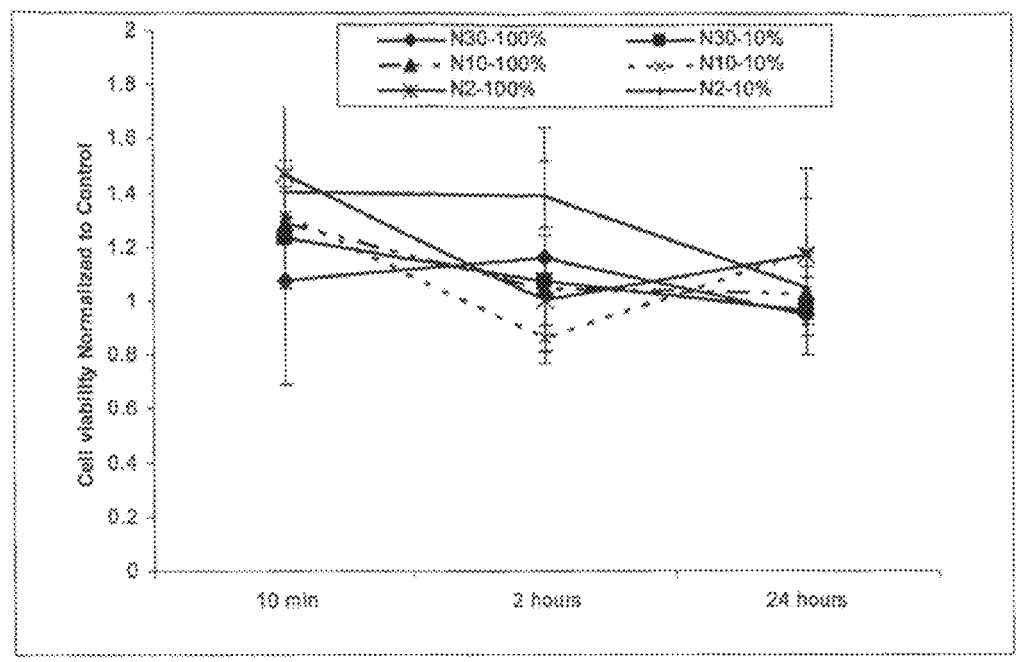
FIG. 17 shows in vitro cytotoxicity of the leachable components from OPF hydrogels.

Viability of the MSCs after 10 minutes, 2 hours and 24 hours exposure to leachable products from hydrogels of different formulations has been shown in FIG. 17. These results show that the leachable products from the prepared hydrogel with no dilution and with 10% dilution did not have adverse effects on viability of the cells.

H. Viability of Photo-Encapsulated Cells

OPF macromer with final concentration of 33% (w/w) was dissolved in PBS containing 0.05% (w/w) Irgacure 2959 (Ciba-Specialty Chemicals) and NVP with different concentrations as previously described (see Table 1). This solution was mixed with $15 \times 10^6$ cells MSCs/ml and pipetted between sterile glass slides with a 1 mm spacer and polymerized using 365 nm UV light at the intensity of ~8 $mW/cm^2$ (Blak-Ray Model 100 AP) for 10 minutes. The resulting hydrogel-cell constructs (5 mm in diameter and 1 mm in thickness) were placed in 12-well tissue culture plate with 2.5 ml MSCs media and incubated in a humid environment with 5% $CO_2$. The constructs were harvested after 1, 7 and 21 days and viability of the encapsulated cells was determined using Live/Dead Viability/Cytotoxicity Kit (Molecular Probes, L3224).

Figure 18:
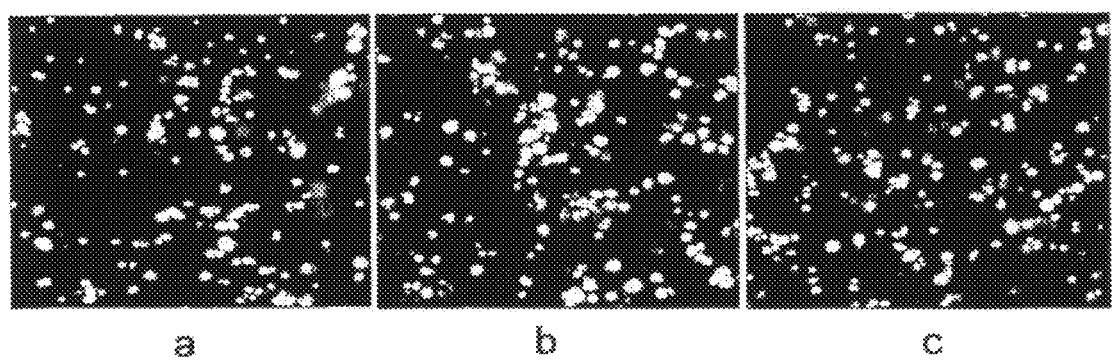
FIG. 18 shows the viability of Marrow stromal cells (MSCs) at (a) 1 day, (b) 7 days, and (c) 21 days after encapsulation.

Viable cells are stained green and dead cells were red when visualized with confocal scanning microscopy. Our results in FIG. 18 showed >95% cell viability after photo-encapsulation and viability remained high after 21 days.

I. Discussion

To guide cartilage tissue regeneration in vivo, cells scaffolds must be designed to provide the initial mechanical and chemical properties needed in the regeneration location, but must simultaneously afford space that increases with time for tissue deposition. In present study, we aimed to accomplish both design requirements by engineering the mechanical and chemical properties of the crosslinked OPF hydrogels. The structural aspects of these OPF networks, especially as a function of degradation rate, were intended to support tissue generation. Our results showed that by varying the percent macromer and NVP crosslinker in solution the gel properties could be significantly varied. As seen in FIGS. 5 and 7, greater swelling ratio was obtained for the hydrogels with lower crosslinking density while the modulus decreased with the decrease in crosslinking density. We also demonstrated that hydrogels degradation rate was correlated with the crosslinking levels. Sol fraction and equilibrium swelling of N5 and N10 samples shown in FIG. 8 increased after 14 days. It appears this increase in the equilibrium swelling is due to the decreased crosslinking density resulting from hydrolysis of the fumarate ester linkages. This hydrolytic degradation can create open spaces for extracellular matrix (ECM) secretion. The modulation of the hydrogels degradation rates offers an opportunity to match the new tissue regeneration rate, and allow appropriate space for tissue ingrowth while maintaining the mechanical properties of the remaining scaffold.

In this study, we hypothesized that hydrogel surface properties affect the cell attachment and morphology. FIG. 9 shows that cell attachment on the hydrogels with higher crosslinking levels was significantly greater than that on the hydrogels with lower crosslinking levels. The behavior of chondrocytes cultured on a specific substrate is detrimental by sequential events starting from integrin mediated interactions with the proteins adsorbed on the biomaterials, subsequent adhesion and morphological changes, regulating the differentiation stage and thus the quality and quantity of ECM deposition. As compared to the other samples, N5 hydrogel with higher swelling ratio, is expected to generate a greater volume of moving water molecules at the scaffold surface which is known to reduce unspecific adsorption of serum proteins, including fibronectin. (See, Genes et al., "Effect of substrate mechanics on chondrocyte adhesion to modified alginate surfaces", *Arch Biochem Biophys* 2004; 422(2):161-7; and Mahmood et al., "Adhesion-mediated signal transduction in human articular chondrocytes: the influence of biomaterial chemistry and tenascin", *C. Exp Cell Res* 2004; 301(2): 179-88.) Round shape morphology on our hydrogels with higher swelling ratio shown in FIG. 8a might be due to a reduced adsorption of fibronectin, protein which is generally associated with cell spreading. The characteristic phenotype of differentiated chondrocytes is that of rounded cells that secrete extracellular matrix proteins (i.e. collagen 11 and aggrecan) and with a diffuse actin microfilament network. Upon attachment to substrates in two dimensions however, chondrocytes have frequently been observed to attain spread morphology with a reorganization of filamentous actin into distinct stress fibers. (See, Genes et al., "Effect of substrate mechanics on chondrocyte adhesion to modified alginate surfaces", *Arch Biochem Biophys* 2004; 422(2):161-7; and Mahmood et al., "Adhesion-mediated signal transduction in human articular chondrocytes: the influence of biomaterial chemistry and tenascin", *C. Exp Cell Res* 2004; 301(2):179-88.) During this dedifferentiation towards a more fibroblastic phenotype, type II collagen production is reduced and eventually replaced with type I collagen, with concomitant reduction or cessation of aggrecan synthesis. Mahmood et al have reported that attached chondrocytes to the polymer substrate containing PEG of different length expressed different phenotypic function. They demonstrated that chondrocytes on TCPS and polymers with short PEG chain had a more fibroblastic phenotype with increased expression of focal adhesion components while actin network in chondrocytes cultured on substrates with longer PEG polymers was diffuse and concentrated towards the cell membrane, indicating that the actin organization remained similar to that of differentiated primary chondrocytes. These findings are in agreement with the trend seen for cell morphology on our OPF hydrogels with varying crosslinking density.

Thus, we have shown that UV light could be used for photocrosslinking of OPF macromer. Hydrogels with different mechanical and swelling behavior were fabricated with the change in concentration of NVP as crosslinking agent. We also shown that hydrogels were degradable and degradation rates varied with the change in crosslinking levels. The change in crosslinking levels appears to modulate chondrocyte attachment and morphology on the OPF hydrogels. Furthermore, viability of the photoencapsulated chondrocytes into the OPF hydrogels was examined. Cell viability remained high after 21 days. This study advances the identification of criteria for design or selection of scaffolds with properties which are instructive for differentiation of chondrocytes and supportive for the generation of three dimensional cartilaginous tissues.

INDUSTRIAL APPLICABILITY

The present invention relates to injectable, photocrosslinkable, biodegradable hydrogels for cell and drug delivery.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A scaffold for tissue regeneration, the scaffold comprising:
    i) a biodegradable matrix comprising a hydrogel comprising oligo(poly(ethylene glycol) fumarate);
    an unsaturated pyrrolidinone monomer; and
    a photoinitiator; wherein the oligo(poly(ethylene glycol) fumarate) is photocrosslinked with the unsaturated pyrrolidinone monomer using the photoinitiator; and
    ii) cells selected from the group consisting of chondrogenic cells and osteogenic cells.
2. The scaffold of claim 1 wherein:
    the cells are encapsulated in the matrix.
3. The scaffold of claim 1 wherein:
    the matrix has a surface and the cells are adhered to the surface of the matrix.
4. The scaffold of claim 3 wherein:
    the cells have a spherical morphology.
5. The scaffold of claim 3 wherein:
    the cells have a flattened morphology.
6. The scaffold of claim 1 wherein:
    the scaffold is porous.
7. The scaffold of claim 6 wherein:
    the hydrogel further comprises a porogen, wherein the oligo(poly(ethylene glycol) fumarate) is photocrosslinked with the unsaturated pyrrolidinone monomer using the photoinitiator in the presence of the porogen.
8. The scaffold of claim 6 wherein:
    the scaffold has a porosity of 70% to 90%.
9. The scaffold of claim 1 wherein:
    the cells are chondrogenic cells.
10. The scaffold of claim 1 wherein:
    the cells are osteogenic cells.
11. The scaffold of claim 1 wherein:
    the cells are suspended in collagen or a collagen derivative selected from the group consisting of gelatin and atelocollagen.
12. The scaffold of claim 1 wherein a weight ratio of oligo(poly(ethylene glycol) fumarate) to pyrrolidinone monomer before the oligo(poly(ethylene glycol) fumarate) is photocrosslinked with the unsaturated pyrrolidinone monomer using the photoinitiator is in the range of 1:0.01 to 1:0.5.
13. The scaffold of claim 1 wherein the unsaturated pyrrolidinone monomer is N-vinyl pyrrolidinone.
14. A method of making a scaffold for tissue regeneration, the scaffold comprising a biodegradable matrix comprising a hydrogel, the method comprising:
    providing cells selected from the group consisting of chondrogenic cells and osteogenic cells;
    providing oligo(poly(ethylene glycol) fumarate) and an unsaturated pyrrolidinone monomer, wherein a weight ratio of the oligo(poly(ethylene glycol) fumarate) to the unsaturated pyrrolidinone monomer is in the range of 1:0.01 to 1:0.5; and
    photocrosslinking the oligo(poly(ethylene glycol) fumarate) and the unsaturated pyrrolidinone monomer using a photoinitiator and the cells.
15. The method of claim 14, the method further comprising:
    selecting the weight ratio of the oligo(poly(ethylene glycol) fumarate) to the unsaturated pyrrolidinone monomer to adjust mechanical properties of the scaffold.
16. The method of claim 14, the method further comprising:
    selecting the weight ratio of the oligo(poly(ethylene glycol) fumarate) to the unsaturated pyrrolidinone monomer to adjust swelling ratio and permeation of the scaffold.
17. The method of claim 14, the method further comprising:
    fabricating a three-dimensional scaffold using stereo-lithography.
18. The method of claim 14 wherein the monomer is N-vinyl pyrrolidinone.

* * * * *

UNITED STATES PATENT AND TRADEMARK OFFICE
CERTIFICATE OF CORRECTION

Page 1 of 1

PATENT NO.          : 8,343,527 B2
APPLICATION NO.     : 11/909241
DATED               : January 1, 2013
INVENTOR(S)         : Mahrokh Dadsetan, Michael J. Yaszemski and Lichun Lu It is certified that error appears in the above-identified patent and that said Letters Patent is hereby corrected as shown below:

In the Specification

Column 1, lines 15-19, please delete the complete paragraph and insert in its place -- This invention was made with government support under AR045871 and EB003060 awarded by the National Institutes of Health. The government has certain rights in the invention. --; thereof.

Signed and Sealed this
Twenty-ninth Day of March, 2016

Michelle K. Lee
*Director of the United States Patent and Trademark Office*